US005928262A

United States Patent [19]
Harber

[11] Patent Number: 5,928,262
[45] Date of Patent: Jul. 27, 1999

[54] HEAD COVERING FOR AT LEAST LIFTING THE FACE OF A WEARER

[76] Inventor: H. Robert Harber, 2417 Ocean Ave., Brooklyn, N.Y. 11229

[21] Appl. No.: 09/053,126

[22] Filed: Apr. 1, 1998

[51] Int. Cl.[6] .......... A61F 5/08

[52] U.S. Cl. .......... 606/204.35; 602/74; 2/206; 601/46

[58] Field of Search .......... 606/204.35; 601/22, 601/38, 46, 117, 151, 166; 602/74; 2/206

[56] References Cited

U.S. PATENT DOCUMENTS

| | | | |
|---|---|---|---|
| 2,134,640 | 10/1938 | Merkin | 606/204.35 |
| 3,557,781 | 1/1971 | Kaye, Sr. | 128/36 |
| 4,239,037 | 12/1980 | Fausone | 128/76 B |
| 4,892,092 | 1/1990 | Klein | 128/76 |
| 4,957,480 | 9/1990 | Morenings | 604/20 |
| 5,067,482 | 11/1991 | Reid | 128/76 B |
| 5,072,724 | 12/1991 | Marcus | 128/66 |
| 5,396,881 | 3/1995 | Klein | 601/23 |
| 5,476,478 | 12/1995 | Jackson | 606/204.35 |

*Primary Examiner*—Michael Buiz
*Assistant Examiner*—Tina T. D. Pham
*Attorney, Agent, or Firm*—Richard L. Miller, P.E.

[57] ABSTRACT

A head covering for at least lifting the face that includes a head covering for covering the entire head and neck and apparatus for simulating the muscles of the head and neck. The head covering has an inner ply for directly overlying the entire head and neck and an outer ply that directly and entirety overlies the inner ply, with both being light weight felt material so as to conform to the entire head and neck without discomfort thereto. The apparatus includes a plurality of vibrators between the inner and outer plies. The plurality of vibrators comprise a forehead vibrator for overlying and vibrating the frontalis muscles, a pair of temple vibrators for overlying and vibrating the temporalis muscles, a pair of under eye vibrators for overlying and vibrating the levator labii superioris muscles, a pair of cheek vibrators for overlying and vibrating the zygomaticus minor and zygomaticus major muscles, a chin vibrator for overlying and vibrating the platysma muscle, and a neck vibrator for overlying and vibrating the auricularis posterior muscle. The plurality of vibrators is one of piezoelectric, electromechanical, and hydrostatic pulsator.

11 Claims, 1 Drawing Sheet

HEAD COVERING FOR AT LEAST LIFTING THE FACE OF A WEARER

BACKGROUND OF THE INVENTION

1. Field of the Invention

The present invention relates to a head covering. More particularly, the present invention relates to a head covering for at least lifting the face of a wearer.

2. Description of the Prior Art

Numerous innovations for facial skin manipulating devices have been provided in the prior art that will be described. Even though these innovations may be suitable for the specific individual purposes to which they address, however, they differ from the present invention.

FOR EXAMPLE, U.S. Pat. No. 4,239,037 to Fausone Leaches face lifting equipment that includes a hairpiece with comb for holding the hairpiece on top of a woman's head. A strip of material including VELCRO is secured at its central portion to the underside of the hairpiece and its top surface made accessible by bending up opposite portions or wing portions of the hairpiece. Elastic bands terminating in adhesive elements include VELCRO pads for connection to the VELCRO on the strip. The adhesive pads adhere to the woman's skin adjacent to her temples to pull upwardly on the skin and thus remove wrinkles and the like. The use of VELCRO provides an infinite number of positions for securement of the VELCRO pads so that a very fine control of the tension in the elastic members can be realized.

ANOTHER EXAMPLE, U.S. Pat. No. 4,957,480 to orenings teaches a method of toning the muscles and tissues of the human face by stimulating the motor nerves and hence cause contractions of the muscles of the human face by applying predetermined galvanic currents, frequencies, and polarities through moistened tips of electrodes continually moistened with a liquid solution of positively and negatively charged particles for introduction into the tissues for nourishment of the muscles and surrounding facial tissues.

STILL ANOTHER EXAMPLE, U.S. Pat. No. 5,067,482 to Reid teaches a device for uplifting facial skin which includes adhesive pads and a nylon line secured over the wearer's head. Upward pulling forces are applied by the line through an elastomeric tension strap which is light or flesh toned color for purposes of concealment. The lower end of the tension strap is releasably mounted to the upward end of a T-bar connector which is formed of a transparent, compliant material. The upper margin of each pad is wrapped over and secured to a crossbar on the lower end of the connector so that the pulling forces are evenly distributed across the width of the pad. When adhering to the facial skin the pad are adjusted to the desired position by a releasable clip through which the nylon line secured.

FINALLY, YET ANOTHER EXAMPLE, U.S. Pat. No. 5,476,478 to Jackson teaches a preoperative skin stretching apparatus and method for preoperatively stretching facial and neck skin to alleviate the complications associated with the extensive undermining of the soft tissues of the face and neck that occur when performing facelifts. The preoperative skin stretching apparatus utilizes a plurality of skin attachments that are sutured superficially to predetermined areas of the skin. A nondistensible headcap is fitted onto a patient's head and covers the rear of the neck and the posterior, superior and frontal areas of the head. A plurality of straps are fixedly attached to the headcap and extend through rectangular apertures provided in the skin attachments. The free end of the straps are pulled rearward toward the headcap in order to pull the skin attachments rearward and apply tension to the skin. The material cooperatively engages to detachably and adjustably maintain the position of the skin attachments and the tension on the skin. Once the spin has stretched, the material on the straps is disengaged, and the free end of the straps is pulled further rearward, along with the skin attachments, to obtain the tension on the skin that was originally applied. After the skin has stretched a desired amount, the headcap and skin attachments are removed, and the facelift procedure is completed.

It is apparent that numerous innovations for facial skin manipulating devices have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a head covering for at least lifting the face of a wearer that avoids the disadvantages of the prior art.

ANOTHER OBJECT of the present invention is to provide a head covering for at least lifting the face of a wearer that is simple and inexpensive to manufacture.

STILL ANOTHER OBJECT of the present invention is to provide a head covering for at least lifting the face of a wearer that is simple to use.

BRIEFLY STATED, YET ANOTHER OBJECT of the present invention is to provide a head covering for at least lifting the face that includes a head covering for covering the entire head and neck and apparatus for simulating the muscles of the head and neck. The head covering has an inner ply for directly overlying the entire head and neck and an outer ply that directly and entirety overlies the inner ply, with both being light weight felt material so as to conform to the entire head and neck without discomfort thereto. The apparatus includes a plurality of vibrators between the inner and outer plies. The plurality of vibrators comprise a forehead vibrator for overlying and vibrating the frontalis muscles, a pair of temple vibrators for overlying and vibrating the temporalis muscles, a pair of under eye vibrators for overlying and vibrating the levator labii superioris muscles, a pair of cheek vibrators for overlying and vibrating the zygomaticus minor and zygomaticus major muscles, a chin vibrator for overlying and vibrating the platysma muscle, and a neck vibrator for overlying and vibrating the auricularis posterior muscle. The plurality of vibrators is one of piezoelectric, electro-mechanical, and hydrostatic pulsator.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures on the drawing are briefly described as follows.

LIST OF REFERENCE NUMERALS UTILIZED IN THE DRAWING

Figure 1:
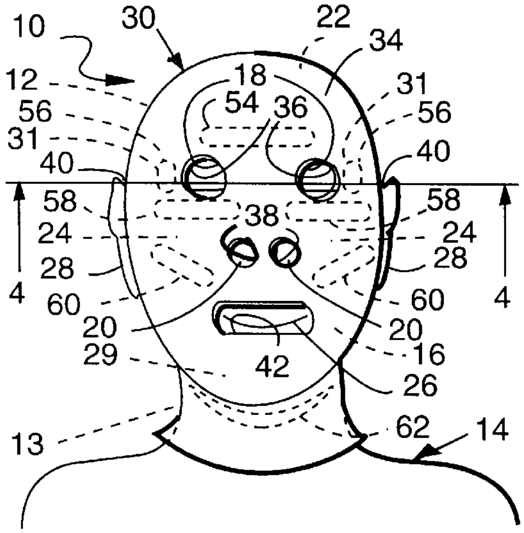
FIG. 1 is a diagrammatic front elevational view of the present invention covering the entire head and neck of a user.
Figure 4:
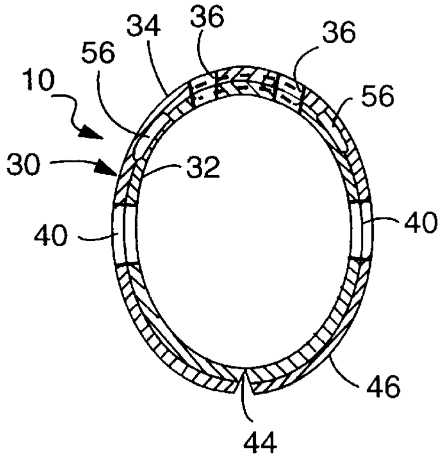
FIG. 4 is a cross sectional view taken on line 4—4 in FIG. 1.

10 head covering for at least lifting the face of a wearer of present invention
12 entire head of wearer 14
13 neck of wearer 14
14 wearer
16 face of wearer 14
18 pair of eyes of wearer 14
20 pair of nostrils of wearer 14
22 forehead of wearer 14
24 pair of cheeks of wearer 14
26 mouth of wearer 14
28 pair of ears of wearer 14
29 chin of wearer 14
30 head covering for covering entire head 12 and neck 13 of wearer 14
31 pair of temples of wearer 14
32 inner ply of head covering 30 for directly overlying entire head 12 and neck 13 of wearer 14
33 nape of neck 13 of wearer 14
34 outer ply of head covering 30
36 pair of eye cut-outs in head covering 30 for aligning with pair of eyes 18 of wearer 14
38 pair of nostril cut-outs in head covering 30 for aligning with pair of nostrils 20 of wearer 14
40 pair of ear cut-outs in head covering 30 for passing pair of ears 28 of wearer 14 therethrough
42 mouth cut-out in head covering 30 for aligning with mouth 26 of wearer 14
44 parting line extending vertically down head covering 30, along its back 46
46 back of head covering 30
48 first strip of hook and loop fasteners
50 second strip of hook and loop fasteners
52 back of neck 13 of wearer 14
54 forehead vibrator or overlying and vibrating frontalis muscle of forehead 22 of wearer 14
56 pair of temple vibrators for overlying and vibrating temporalis muscles of pair of temples 31 of wearer 14
58 pair of under eye vibrators for overlying and vibrating levator labii superioris muscles of face 16 of wearer 14, under pair of eyes 18 of wearer 14
60 pair of cheek vibrators for overlying and vibrating zygomaticus minor and zygomaticus major muscles of pair of cheeks 24 of wearer 14
62 chin vibrator for overlying and vibrating platysma muscle of chin 29 of wearer 14
63 neck vibrator for overlying and vibrating auricularis posterior muscle of nape 33 of neck 13 of wearer 14
64 controller
66 conductor
68 switch
70 power source

DETAILED DESCRIPTION OF THE PREFERRED EMBODIMENT

Figure 2:
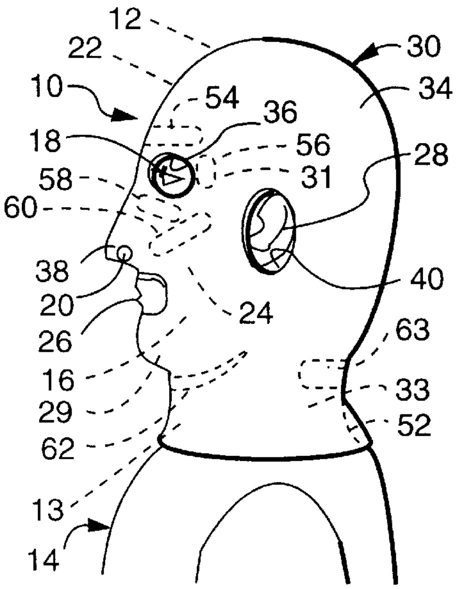
FIG. 2 is a diagrammatic side elevational view of the present invention covering the entire head and neck of a user.
Figure 3:
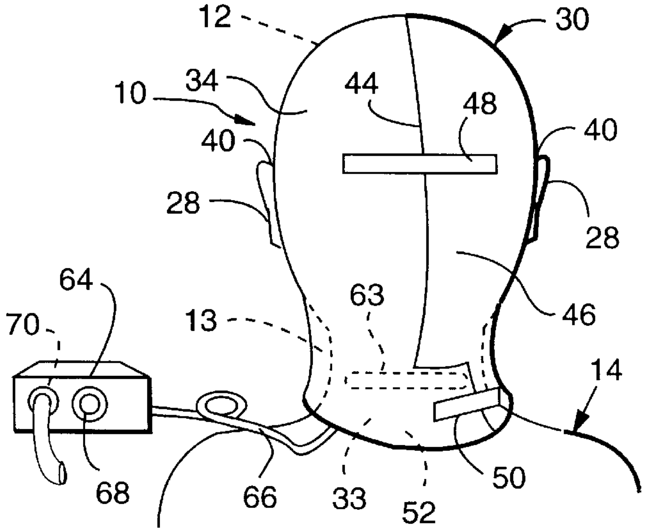
FIG. 3 is a diagrammatic rear elevational view of the present invention covering the entire head and neck of a user.

Referring now to the figures in which like numerals indicate like parts, and particularly to FIGS. 1–3, the head covering for at least lifting the face of a wearer of the present invention is shown generally at 10 for covering the entire head 12 and neck 13 of a wearer 14 and at least lifting the face 16 of the wearer 14, wherein the wearer 14 further has a pair of eyes 18, a pair of nostrils 20, a forehead 22, a pair of cheeks 24, a mouth 26, a pair of ears 28, a chin 29, and a pair of temples 31, and the neck 13 of the wearer has a nape 33.

The configuration of the head covering for at least lifting the face of a wearer 10 can best be seen in FIGS. 1–4, and as such, will be discussed with reference thereto.

The head covering for at least lifting the face of a wearer 10 comprises a head covering 30 for covering the entire head 12 and neck 13 of the wearer 14, and has an inner ply 32 for directly overlying the entire head 12 and neck 13 of the wearer 14 and an outer ply 34 that directly overlies the inner ply 32 of the head covering 30, in its entirety.

The inner ply 32 of the head covering 30 and the outer ply 34 of the head covering 30 are both light weight felt material so as to conform to the entire head 12 and neck 13 of the wearer 14 without discomfort thereto.

The head covering 30 has a pair of eye cut-outs 36 therein for aligning with the pair of eyes 18 of the wearer 14 so as to allow the wearer 14 to see therethrough, a pair of nostril cut-outs 38 therein for aligning with the pair of nostrils 20 of the wearer 14 so as to allow the wearer 14 to breathe therethrough, a pair of ear cut-outs 40 therein for passing the pair of ears 28 of the wearer 14 therethrough so as to allow the wearer 14 to hear, and a mouth cut-out 42 therein for aligning with the mouth 26 of the wearer 14 so as to allow the wearer 14 to talk therethrough.

The head covering 30 further has a parting line 44 that extends vertically down the head covering 30, along its back 46, so as to allow the head covering 30 to have a worn position where it directly overlies the entire head 12 and neck 13 of the wearer 14 and a removed position where it is opened at the parting line 44 in the back 46 of the head covering 30 and removed from the entire head 12 and neck 13 of the wearer 14.

The head covering 30 is maintained in the worn position by a first strip of hook and loop fasteners 48 that is disposed on the back 46 of the head covering 30 and overlaps the parting line 44 in the head covering 30 and a second strip of hook and loop fasteners 50 that is disposed on the head covering 30 over the neck 13 of the wearer 14, at is back 52, and overlaps the parting line 44 in the head covering 30.

The head covering for at least lifting the face of a wearer 10 further comprises a plurality of vibrators, whose positioning will be discussed infra, that are disposed between the inner ply 32 of the head covering 30 and the outer ply 34 of the head covering 30, at specific positions therebetween for overlying and vibrating specific portions of the entire head 12 and neck 13 of the wearer 14.

The plurality of vibrators comprise a forehead vibrator 54 for overlying and vibrating the frontalis muscles of the forehead 22 of the wearer 14.

The plurality of vibrators further comprise a pair of temple vibrators 56 for overlying and vibrating the temporalis muscles of the pair of temples 31 of the wearer 14.

The plurality of vibrators further comprise a pair of under eye vibrators 58 for overlying and vibrating the levator labii superioris muscles of the face 16 of the wearer 14, under the pair of eyes 18 of the wearer 14.

The plurality of vibrators further comprise a pair of cheek vibrators 60 for overlying and vibrating the zygomaticus minor and zygomaticus major muscles of the pair of cheeks 24 of the wearer 14.

The plurality of vibrators further comprise a chin vibrator 62 for overlying and vibrating the platysma muscle of the chin 29 of the wearer 14.

The plurality of vibrators further comprise a neck vibrator 63 for overlying and vibrating the auricularis posterior muscle of the nape 33 of the neck 13 of the wearer 14.

The plurality of vibrators is in communication with a controller 64, by a conductor 66, with a switch 68 therebetween determining when power from a power source 70 flows to the controller 64.

The plurality of vibrators is one of piezoelectric, electromechanical, and hydrostatic pulsator, with the controller 64 being a hydro-electric pump when the plurality of vibrators are hydrostatic pulsator.

It will be understood that each of the elements described above, or two or more together, may also find a useful application in other types of constructions differing from the types described above.

While the invention has been illustrated and described as embodied in a head covering for lifting at least the face of a wearer, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A head covering for at least lifting the face of a wearer, comprising:

a) a head covering for covering the head and neck of the wearer; said head covering covering the head of the wearer, in its entirety; said head covering having an inner ply for directly overlying the entire head and neck of the wearer and an outer ply directly overlying said inner ply of said head covering, in its entirety; said inner ply of said head covering and said outer ply of said head covering being both light weight felt material so as to conform to the entire head and neck of the wearer without discomfort thereto; said head covering further having a pair of ear cut-outs therein for passing the pair of ears of the wearer therethrough so as to allow the wearer to hear; said head covering further having a parting line extending vertically down said head covering, along its back, so as to allow said head covering to have a worn position where it directly overlies the entire head and neck of the wearer and a removed position where it is opened at said parting line in said back of said head covering and removed from the entire head and neck of the wearer; said head covering maintained in said worn position by a first strip of hook and loop fasteners disposed on said back of said head covering and overlapping said parting line in said head covering and a second strip of hook and loop fasteners disposed on said head covering over the neck of the wearer, at its nape, and overlapping said parting line in said head covering; and b) means for simulating the muscles of the head and neck of the wearer; said means including a plurality of vibrators disposed between said inner ply of said head covering and said outer ply of said head covering, at specific positions therebetween for overlying and vibrating specific portions of the entire head and neck of the wearer; said plurality of vibrators comprising a forehead vibrator for overlying and vibrating the frontalis muscles of the forehead of the wearer.

2. The covering as defined in claim 1, wherein said head covering has a pair of eye cut-outs therein for aligning with the pair of eyes of the wearer so as to allow the wearer to see therethrough.

3. The covering as defined in claim 1, wherein said head covering further has a pair of nostril cut-outs therein for aligning with the pair of nostrils of the wearer so as to allow the wearer to breathe therethrough.

4. The covering as defined in claim 1, wherein said head covering further has a mouth cut-out therein for aligning with the mouth of the wearer so as to allow the wearer to talk therethrough.

5. The cover as defined in claim 1, wherein said plurality of vibrators further comprise a pair of temple vibrators for overlying and vibrating the temporalis muscles of the pair of temples of the wearer.

6. The cover as defined in claim 1, wherein said plurality of vibrators further comprise a pair of under eye vibrators for overlying and vibrating the levator labii superioris muscles of the face of the wearer, under the pair of eyes of the wearer.

7. The cover as defined in claim 1, wherein said plurality of vibrators further comprise a pair of cheek vibrators for overlying and vibrating the zygomaticus minor and zygomaticus major muscles of the pair of cheeks of the wearer.

8. The cover as defined in claim 1, wherein said plurality of vibrators further comprise a chin vibrator for overlying and vibrating the platysma muscle of the chin of the wearer.

9. The cover as defined in claim 1, wherein said plurality of vibrators further comprise a neck vibrator for overlying and vibrating the auricularis posterior muscle of the nape of the neck of the wearer.

10. The cover as defined in claim 1, wherein said plurality of vibrators is in communication with a controller, by a conductor, with a switch therebetween determining when power from a power source flows to said controller.

11. The cover as defined in claim 10, wherein said plurality of vibrators is one of piezoelectric, electromechanical, and hydrostatic pulsator, with said controller being a hydro-electric pump when said plurality of vibrators are hydrostatic pulsator.

* * * * *